United States Patent [19]

Yoshida et al.

[11] 4,144,049

[45] Mar. 13, 1979

[54] N-(4-BENZYLOXYPHENYL)-N-METHYL-N-METHOXYUREA

[75] Inventors: Ryo Yoshida, Kawanishi; Seizo Sumida, Nishinomiya; Eiyoshi Itooka, Takarazuka; Hiroshi Noguchi; Katsuzo Kamoshita, both of Toyonaka, all of Japan

[73] Assignee: Sumitomo Chemical Company, Limited, Osaka, Japan

[21] Appl. No.: 773,784

[22] Filed: Mar. 2, 1977

[30] Foreign Application Priority Data

Mar. 16, 1976 [JP] Japan .................................. 51-28999

[51] Int. Cl.² ............................................. A01N 9/20
[52] U.S. Cl. ............................. 71/120; 260/453 RW
[58] Field of Search ................... 260/453 RW; 71/120

[56] References Cited

FOREIGN PATENT DOCUMENTS 507646  7/1971  Switzerland.
532891  3/1973  Switzerland ...................... 260/453 RW

*Primary Examiner*—Joseph Paul Brust
*Attorney, Agent, or Firm*—Birch, Stewart, Kolasch and Birch

[57] ABSTRACT

N-(4-Benzyloxyphenyl)-N'-methyl-N'-methoxyurea of the formula:

which shows a pronounced herbicidal activity against weeds in the cultivation of soybean without any material toxicity to mammals and soybean plants.

4 Claims, No Drawings

N-(4-BENZYLOXYPHENYL)-N'-METHYL-N'-METHOXYUREA

This present invention relates to N-(4-benzyloxyphenyl)-N'-methyl-N'-methoxyurea of the formula:

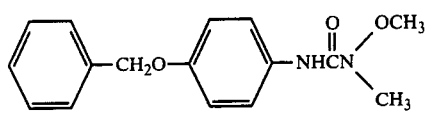

which shows a pronounced herbicidal activity against weeds in the cultivation of soybean without damaging the soybean crop, and its preparation and use.

Soybean is one of the crops of world-wide importance as a source of oil or vegetable protein. Since soybean is a crop, the yield of which is easily reduced by weeds, the control of weeds is essential to the cultivation of soybean. Such control has been achieved by the use of herbicides from the standpoint of saving labor.

The principal herbicides presently used in the cultivation of soybean are of the soil-application type and their application is made before germination of the weeds so that the period during which the herbicidal activity is maintained is limited to the very early stage of the culture. Accordingly, a foliar-applied herbicide which can be applied later, that is, at the growing stage of weeds is desirable. But the fact is that the herbicides of this type now in practical use are limited in kind and, moreover, that those are frequently limited in application time and application method because of the phytotoxicity to the soybean crop. For example, chloroxuron (i.e., N'-[4-(4-chlorophenoxy)phenyl]-N,N-dimethylurea) and bentazon (i.e., 3-isopropyl-1H-2,1,3-benzothiadiazin-4-(3H)-one-2,2-dioxide) are in practical use as selective foliar-applied herbicides in the cultivation of soybean crops. Chloroxuron, however, tends to exhibit a considerable phytotoxicity to the soybean crop at the unifoliar to early trifoliar leaf stage by over-the-top post-emergence application. Therefore, it has a limitation as to the timing of its application. Bentazon does not exhibit a sufficient herbicidal efficacy against grassy weeds in general, and moreover, it does not exhibit a satisfactory efficacy against some important broad-leaved weeds in the cultivation of soybean crops, such as pigweed and morning glory. Therefore, it can be said that bentazon is not suitable for controlling these weed species.

As the result of the study seeking a foliar-applied herbicide having a high selectivity on soybean, that is, having a strong herbicidal activity without damaging the soybean crop and moreover without being so limited in the timing of its application, it has now been found that N-(4-benzyloxyphenyl)-N'-methyl-N'-methoxyurea (hereinafter referred to as "invention compound [I]") is quite suitable for the said purpose.

N-(4-Benzyloxyphenyl)-N',N'-dimethylurea (hereinafter referred to as "control compound (1)") has the following formula:

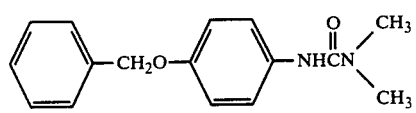

which is similar to that of the invention compound [I]. This compound is disclosed to be useful as a herbicidal agent in Japanese Patent Publication (unexamined) No. 2269/1971. In the disclosure of this patent publication, however, it is described to possess no selectivity to soybean crops.

On the other hand, the invention compound [I] is generically disclosed in Swiss Pat. No. 532,891. In that patent, however, no specific description on the invention compound [I] is given. Moreover, that patent is entirely silent on the selectivity to soybean crops. Among the specifically described compounds in that patent, those having a similar chemical structure to that of the invention compound [I] are N-(3-chloro-4-benzyloxyphenyl)-N'-methyl-N'-methoxyurea (hereinafter referred to as "control compound (2)") of the following formula:

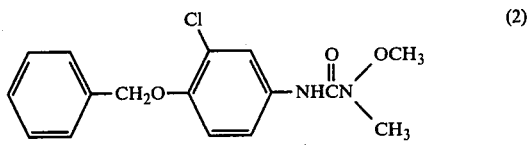

and N-(4-phenoxyphenyl)-N'-methyl-N'-methoxyurea (hereinafter referred to as "control compound (3)") of the following formula:

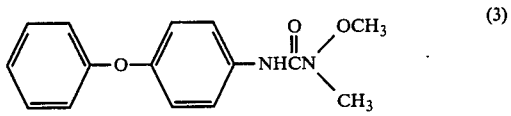

which exhibit a particularly strong phytotoxicity to soybean crops. As is hereinafter shown in Examples I and II, however, these control compounds (1), (2) and (3) have scarcely any selectivity to a soybean crop. Thus, they kill the soybean crop when applied at such dosage rates at which they exhibit sufficient herbicidal activity to weeds.

The invention compound [I] shows strong herbicidal activities against a wide range of weeds such as redroot pigweed (*Amaranthus retroflexus*), common lambsquarter (*Chenopodium album*), cocklebur sp. (*Xanthium strumarium*), chickweed (*Stellaria media*), mouseear chickweed (*Cerastium viscosum*), starwort sp. (*Stellaria alsine*), bitter cress sp. (*Cardamine flexuosa*), pale smartweed (*Polygonum lapathifolium*), common purslane (*Portulaca oleracea*), large crabgrass (*Digitaria sanguinalis*), barnyard grass (*Echinochloa crus-galli*), annual bluegrass (*Poa annua*), green foxtail (*Setaria viridis*), nutsedge sp. (*Cyperus diffomis*) and the like in their growing stage. Furthermore, the invention compound [I] is characteristically superior in that it can be applied to the soybean crop with an extremely high safety. For example, when it is used at the usual herbicidally effective dosage rate between 2.5 g per are and 40 g per are, it can be applied to the foliage over the top at any stage of the growing period of the soybean crop without damaging it. Further, even if the dosage rate becomes higher, it causes only a slight damage to the soybean crop and is essentially non-toxic to the soybean crop.

Among the conventionally used herbicides, those exhibiting such a remarkable selectivity over a wide range of dosage rate are very rare. Consequently, the present invention is particularly notable in providing a compound having such a remarkable selectivity to soybean crops which is one of the most important crops in the world.

The invention compound [I] is novel and can be synthesized by various methods such as, for example, the three methods as described below.

The first method comprises the reaction between 4-benzyloxyphenyl isocyanate [II] and N,O-dimethylhydroxylamine [III], which is representable by the formula:

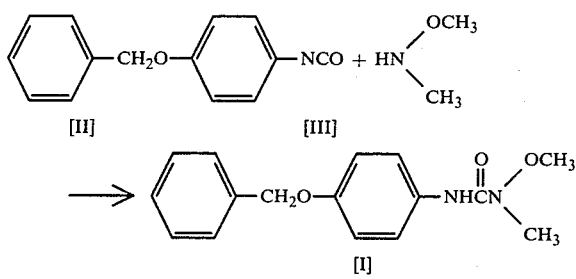

The reaction is usually carried out in an inert solvent at room temperature. For example, a solution of N,O-dimethylhydroxylamine [III] in benzene is added dropwise to a solution of 4-benzyloxyphenyl isocyanate [II] in benzene at room temperature, the amounts of the compounds [II] and [III] being equimolar. Thereafter, the mixture is stirred for 1 hour, and the solvent is then removed by evaporation to obtain the invention compound [I] in a high yield.

The second method comprises the reaction between 4-benxyloxyphenylcarbamyl halide [IV] and N,O-dimethylhydroxylamine [III], which is representable by the formula:

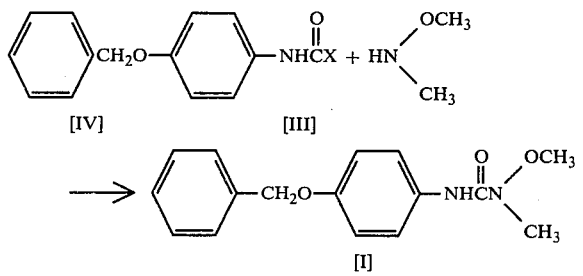

wherein X is a halogen atom (e.g., chlorine, bromine).

Usually, the reaction is carried out in an inert solvent under reflux. The presence of an acid-eliminating agent such as an organic base in the reaction system is generally preferred. For example, a mixture of N,O-dimethylhydroxylamine [III] and triethylamine is added dropwise to a solution of 4-benzyloxyphenylcarbamyl halide [IV] in benzene, the amounts of the compounds [III] and [IV] and triethylamine being equimolar. The resulting mixture is refluxed for 2 hours and cooled to room temperature. The by-produced triethylamine hydrochloride is eliminated with addition of water, and the solvent is then removed by evaporation to obtain the invention compound [I] in a high yield.

The third method comprises the reaction between N-(4-hydroxyphenyl)-N'-methyl-N'-methoxyurea [V] and benzyl halide [VI], which is representable by the formula:

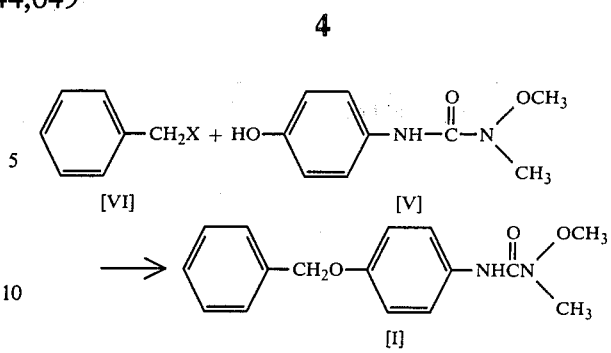

wherein X is as defined above.

Usually, the reaction is carried out in an inert solvent under reflux. The presence of an acid-eliminating agent such as an inorganic base in the reaction system is generally favorable. For example, benzyl halide [VI] is added to a solution of N-(4-hydroxyphenyl)-N'-methyl-N'-methoxyurea [V] in benzene and a 50% aqueous solution of sodium hydroxide is added thereto, the amounts of the compounds [V] and [VI] and sodium hydroxide being equimolar. The mixture is heated under reflux and washed with water, followed by removal of the solvent by evaporation to obtain the invention compound [I] in a high yield.

In the actual application as a herbicide, the invention compound [I] may be used alone without incorporation of any other ingredient such as a carrrier or a diluent, but for easier application, it may be used in admixture with such solid carriers or diluents as talc, bentonite, clay, kaolin, diatomaceous earth, vermiculite, slaked lime and the like or with such liquid carriers or diluents as water, benzene, alcohols, acetone, xylene, methylnaphthalene, dioxane, cyclohexanone, dimethylformamide, ethyl acetate, acetonitrile and the like. The herbicidal composition can be formulated into any of the ordinarily adopted forms such as, for example, dusts, wettable powders, oil sprays, aerosols, tablets, emulsifiable concentrates, granules and fine granules. Further, the invention compound [I] may be used in admixture with other herbicides, microbial pesticides, pyrethroid type or other insecticides, fungicides, fertilizers, etc.

Practical and presently preferred embodiments of the present invention are illustratively shown in the following examples, wherein parts and % are by weight.

EXAMPLE 1

Preparation of the invention compound [I]:

To a solution of 22.5 g of 4-benzyloxyphenyl isocyanate in 60 ml of benzene, a solution of 12 g of N,O-dimethylhydroxylamine in 60 ml of benzene is added dropwise at a temperature of 20° to 30° C. After the addition is over, the reaction mixture is continuously stirred at the same temperature for an additional 30 minutes. The solvent is removed under reduced pressure to obtain 24 g of crystals. Recrystallization from methanol is carried out twice to obtain 12 g of N-(4-benzyloxyphenyl)-N'-methyl-N''-methoxyurea as white needle-like crystals. M.P. 104.5°–105° C.

Elementary analysis: Calcd. for $C_{16}H_{18}N_2O_3$: C, 67.10%; H, 6.35%; N, 9.78%. Found: C, 66.85%; H, 6.36%; N, 9.72%.

EXAMPLE 2

Formulation of herbicidal compositions:

(a) Wettable powder

Fifty parts of the invention compound [I], 5 parts of a wetting agent (alkylbenzene sulfonate type) and 45 parts of diatomaceous earth are well mixed while being powdered. Thus, a wettable powder is obtained.

(b) Emulsifiable concentrate

Twenty parts of the invention compound [I], 30 parts of cyclohexanone, 30 parts of dimethylformamide and 20 parts of polyethylene glycol ether are well mixed to obtain an emulsifiable concentrate.

(c) Dust

Ten parts of the invention compound [I] and 90 parts of clay are well mixed while being powdered. Thus, a dust is obtained.

When the invention compound [I] is applied as a herbicide, the application method and the dosage rate depend upon the type of formulation of the compound, the kinds of weeds to be killed and weather conditions. It is preferably applied to both weeds and soybean crops over the top in the post-emergence treatment, but it may be applied at any time ranging from the stage immediately after sowing to the third trifoliate leaf stage of the soybean crop. The dosage rate is generally about 2 g to about 80 g, preferably 5 g to 40 g, of the active ingredient per are.

The following examples show some typical test data indicating the excellent herbicidal activity of the invention compound [I].

at 25° C. for 19 days in a green-house. Radish, sunflower, soybean and corn were similarly grown for 12 days. Thus, the test plants were prepared. The test compound was formulated into a 20% emulsifiable concentrate according to the preparation method as described in Example 2 b) and diluted with water containing a wetting agent to give a spray volume of 10 liters/are. The test solution thus prepared was sprayed to the foliage of the test plants over the top by means of a small hand sprayer. After spraying, the test plants were further grown for 23 days in the green-house to check the herbicidal activity. The degree of phytotoxicity and the survival rate of the test plants were checked, and the herbicidal activity of the test compound was rated on a scale of 0 to 5 based on the following standard:

| Rating value | Degree of phytotoxicity | Fresh weight (%) |
|---|---|---|
| 0 | No | 100 |
| 1 | Slight (plants recovered from phytotoxicity) | 80–99 |
| 2 | Low | 50–79 |
| 3 | Moderate | 20–49 |
| 4 | High | 1–19 |
| 5 | Complete death | 0 |

The results are shown in Table 1.

Table 1:

| Test compound | Dosage rate (weight of active ingredient (g/are) | Redroot pigweed 2-leaf stage 3 cm | Common lambsquarter 4-leaf stage 2 cm | Radish 1-leaf stage 5 cm | Sunflower 2-leaf stage 15 cm | Cocklebur 2-leaf stage 6 cm | Cotton cotyledon stage 7 cm | Soybean primary leaf stage 12 cm | Barnyard grass 2-leaf stage 7 cm | Large crabgrass 2.5-leaf stage 6 cm | Corn 2.5-leaf stage 20 cm |
|---|---|---|---|---|---|---|---|---|---|---|---|
| Invention compound [I] | 40 | 5 | 5 | 5 | 5 | 5 | 5 | 1 | 5 | 5 | 5 |
| | 20 | 5 | 5 | 5 | 5 | 5 | 5 | 0 | 5 | 5 | 5 |
| | 10 | 5 | 5 | 5 | 5 | 5 | 5 | 0 | 5 | 5 | 5 |
| | 5 | 5 | 5 | 5 | 5 | 5 | 5 | 0 | 5 | 5 | 5 |
| | 2.5 | 5 | 5 | 5 | 5 | 4 | 5 | 0 | 5 | 5 | 5 |
| Control compound (1) | 40 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| | 10 | 5 | 5 | 5 | 5 | 5 | 5 | 4 | 5 | 5 | 5 |
| | 5 | 5 | 5 | 5 | 5 | 4 | 5 | 4 | 4 | 4 | 4 |
| | 2.5 | 5 | 5 | 5 | 4 | 4 | 5 | 3 | 3 | 4 | 4 |
| Control compound (2) | 40 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| | 10 | 5 | 5 | 5 | 5 | 5 | 5 | 5 | 5 | 5 | 4 |
| | 5 | 5 | 5 | 5 | 5 | 5 | 5 | 5 | 5 | 4 | 4 |
| | 2.5 | 5 | 5 | 5 | 4 | 4 | 5 | 5 | 4 | 4 | 3 |
| Control compound (3) | 40 | 5 | 5 | 5 | 5 | 5 | 5 | 5 | 4 | 5 | 5 |
| | 20 | 5 | 5 | 5 | 5 | 5 | 5 | 5 | 4 | 4 | 5 |
| | 10 | 5 | 5 | 5 | 5 | 5 | 5 | 4 | 3 | 4 | 5 |
| | 5 | 5 | 5 | 4 | 4 | 4 | 4 | 2 | 2 | 2 | 4 |
| | 2.5 | 5 | 4 | 2 | 3 | 3 | 3 | 2 | 1 | 0 | 3 |
| Bentazon | 40 | 5 | 5 | 5 | 5 | 5 | 5 | 2 | 3 | 2 | 2 |
| | 20 | 4 | 5 | 5 | 5 | 5 | 5 | 1 | 2 | 1 | 1 |
| | 10 | 3 | 5 | 5 | 5 | 5 | 5 | 0 | 0 | 0 | 1 |
| | 5 | 3 | 5 | 5 | 5 | 5 | 5 | 0 | 0 | 0 | 0 |
| | 2.5 | 2 | 5 | 5 | 5 | 5 | 3 | 0 | 0 | 0 | 0 |
| Chloroxuron | 40 | 5 | 5 | 5 | 5 | 5 | 5 | 5 | 5 | 5 | 5 |
| | 20 | 5 | 5 | 5 | 5 | 5 | 5 | 4 | 5 | 5 | 5 |
| | 10 | 5 | 5 | 5 | 5 | 5 | 5 | 3 | 5 | 5 | 5 |
| | 5 | 5 | 5 | 5 | 5 | 5 | 5 | 2 | 5 | 5 | 5 |
| | 2.5 | 5 | 5 | 5 | 5 | 4 | 5 | 2 | 3 | 5 | 5 |

EXAMPLE I

Herbicidal activity by foliage treatment and phytotoxicity:

Plastic pots (0.1 m²) were filled with field soil, and the seeds of redroot pigweed (*Amaranthus retroflexus*), common lambsquarter (*Chenopodium album*), cocklebur (*Xanthium strumarium*), cotton, barnyard grass (*Echinochloa crus-galli*) and large crabgrass (*Digitaria sanguinalis*) were sowed in each of the pots and grown

EXAMPLE II

Phytotoxicity to soybean:

1/5,000 (ares) Wagner's pots were filled with field soil, and the seeds of soybean were sowed and grown at 25° C. in a green-house. The soybean plants were grown to the different growing stages (i.e. a primary leaf stage, a first trifoliate leaf stage and a second trifoliate leaf stage) and used for the test.

The test compound was formulated into a 20% emulsifiable concentrate according to the preparation method as described in Example 2 (b) and diluted with water containing a wetting agent to give a spray volume of 10 liters/are. The test solution thus prepared was sprayed to the foliage of the test plants over the top by means of a small hand sprayer. After spraying, the test plants were further grown for 25 days in the greenhouse. The phytotoxicity to soybean was rated on the scale of 0 to 5 according to the criteria in Example I.

The results are shown in Table 2.

Table 2

| Test compound | Dosage rate (weight of active ingredient (g/are)) | Growing stage and plant height at the foliage treatment | | |
|---|---|---|---|---|
| | | Primary leaf stage 11 cm | First trifoliate leaf stage 14 cm | Second trifoliate leaf stage 17 cm |
| Invention compound [I] | 40 | 1 | 0 | 0 |
| | 20 | 0 | 0 | 0 |
| | 10 | 0 | 0 | 0 |
| | 5 | 0 | 0 | 0 |
| Control compound (1) | 40 | 5 | 5 | 5 |
| | 20 | 5 | 4 | 4 |
| | 10 | 4 | 3 | 3 |
| | 5 | 4 | 3 | 2 |
| Control compound (2) | 40 | 5 | 5 | 5 |
| | 20 | 5 | 5 | 5 |
| | 10 | 5 | 5 | 5 |
| | 5 | 5 | 5 | 4 |
| Control compound (3) | 40 | 5 | 4 | 4 |
| | 20 | 5 | 4 | 3 |
| | 10 | 4 | 3 | 3 |
| | 5 | 3 | 2 | 1 |
| Bentazon | 40 | 1 | 0 | 0 |
| | 20 | 1 | 0 | 0 |
| | 10 | 0 | 0 | 0 |
| | 5 | 0 | 0 | 0 |
| Chloroxuron | 40 | 5 | 3 | 3 |
| | 20 | 4 | 3 | 2 |
| | 10 | 3 | 2 | 2 |
| | 5 | 3 | 2 | 1 |

EXAMPLE III

Herbicidal activity to weeds at different growing stages.:

1/5,000 (ares) Wagner's pots were filled with upland soil, and the seeds of large crabgrass (*Digitaria sanguinalis*) and redroot pigweed (*Amaranthus retroflexus*) were sowed and grown at 25° C. in a green-house.

The invention compound [I] was formulated into a 20% emulsifiable concentrate according to the preparation method as described in Example 2 (b) and diluted with water containing a wetting agent to give a spray volume of 10 liters/are. The test solution thus prepared was applied to the soil surface immediately after the sowing, or over the foliage of the large crabgrass grown to the heights of 6 cm, 11 cm, 15 cm or 20 cm. In this way, the relationship between the growing stage of the weeds and the herbicidal activity was examined.

These growing stages of the weeds correspond to those of soybean, namely, the stage immediately after sowing, primary leaf stage, first, second and third trifoliate leaf stages, respectively. Twenty-five days after the foliage treatment, the herbicidal activity was rated on the scale of 0 to 5 according to the criteria in Example I.

The results are shown in Table 3.

Table 3

| Test compound | Dosage rate (weight of active ingredient (g/are)) | Test plant and plant height at the foliage treatment (cm) | | | | | | | | | |
|---|---|---|---|---|---|---|---|---|---|---|---|
| | | Large crabgrass | | | | | Redroot pigweed | | | | |
| | | 0 | 6 | 11 | 15 | 20 | 0 | 3 | 4 | 5 | 7 |
| Invention compound [I] | 40 | 5 | 5 | 5 | 5 | 5 | 5 | 5 | 5 | 5 | 5 |
| | 20 | 5 | 5 | 5 | 5 | 5 | 5 | 5 | 5 | 5 | 5 |
| | 10 | 5 | 5 | 5 | 5 | 4 | 5 | 5 | 5 | 5 | 5 |
| | 5 | 5 | 5 | 5 | 4 | 4 | 5 | 5 | 5 | 5 | 5 |

What is claimed is:

1. A method of selectively combating weeds in the cultivation of soybean without any material phytotoxicity to the soybean plants which comprises applying to both the weeds and the soybean crop over the top in a post-emergence treatment a herbicidal compound of the formula:

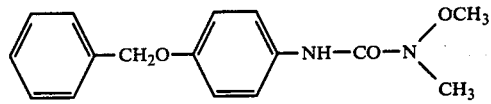

in a dosage rate of about 2 to about 80 grams per are.

2. The method of claim 1, wherein the dosage rate of said herbicidal compound is about 5 to 40 grams per are.

3. The method of claim 1, wherein said compound is applied in the form of a herbicidal composition comprising said compound and an inert carrier.

4. The method of claim 1, wherein said compound is applied to the foliage over the top at any stage of the growing period of the soybean crop.

* * * * *